US007003123B2

(12) United States Patent
Kanevsky et al.

(10) Patent No.: US 7,003,123 B2
(45) Date of Patent: Feb. 21, 2006

(54) VOLUME REGULATING AND MONITORING SYSTEM

(75) Inventors: Dimitri Kanevsky, Ossining, NY (US); Wlodek W. Zadrozny, Tarrytown, NY (US); Sarah H. Basson, White Plains, NY (US)

(73) Assignee: International Business Machines Corp., Armonk, NY (US)

( * ) Notice: Subject to any disclaimer, the term of this patent is extended or adjusted under 35 U.S.C. 154(b) by 610 days.

(21) Appl. No.: 09/892,804

(22) Filed: Jun. 27, 2001

(65) Prior Publication Data

US 2003/0002688 A1 Jan. 2, 2003

(51) Int. Cl.
*A61F 11/06* (2006.01)

(52) U.S. Cl. .......................................... 381/72; 381/74

(58) Field of Classification Search .................. 381/72, 381/74, 58, 56, 309, 104, 105, 106, 107, 381/109

See application file for complete search history.

(56) References Cited

U.S. PATENT DOCUMENTS

| | | | | |
|---|---|---|---|---|
| 4,061,875 | A * | 12/1977 | Freifeld et al. | 381/72 |
| 4,538,296 | A * | 8/1985 | Short et al. | 381/72 |
| 5,046,101 | A * | 9/1991 | Lovejoy | 381/57 |
| 5,317,273 | A * | 5/1994 | Hanson et al. | 381/58 |
| 5,771,441 | A * | 6/1998 | Altstatt | 381/309 |
| 6,061,431 | A * | 5/2000 | Knappe et al. | 379/52 |
| 6,567,524 | B1 * | 5/2003 | Svean et al. | 381/72 |

* cited by examiner

*Primary Examiner*—Ping Lee
(74) *Attorney, Agent, or Firm*—Satheesh Karra, Esq.

(57) ABSTRACT

A volume controlling system and method for regulating the output volume of a headset in order to protect the hearing ability of a user. The system includes a volume sensor/controller for monitoring the volume output of the headset by adjusting the volume to be within a predetermined threshold. A warning indicator indicates to the user or a person monitoring the listening user that the volume is set too high. The method include the steps of comparing the received audio signal to the predetermined volume threshold and adjusting the volume accordingly. The method also includes the steps of notifying that the volume has been set at too high a level by providing a warning signal, such as an audible or visual alarm.

15 Claims, 3 Drawing Sheets

VOLUME REGULATING AND MONITORING SYSTEM

FIELD OF THE INVENTION

The present invention relates generally to a volume regulating and monitoring system, and in particular, to a system and method of regulating and monitoring volume in a headset by adjusting the volume according to predetermined thresholds and signaling when the predetermined thresholds have been exceeded.

BACKGROUND OF THE INVENTION

Many children and adolescents experience hearing problems because of listening to music, watching television and movies, and playing with video games and toys that are very loud. Currently, some solutions to this problem are the use of headphones, and in particular, headphones having volume limitation mechanisms. Unfortunately, these solutions still require constant supervision. A volume limiter can also be a useful solution, but may become frustrating to use if the volume is set too low and the user cannot hear the audio, or ineffective if the volume is set too high.

SUMMARY

It is, therefore, an aspect of the present invention to provide a system for controlling a volume output of headphones to prevent harmful sound levels from damaging a user's hearing.

It is another aspect of the present invention to provide a monitoring system to monitor the user's listening habits and track the user's listening history.

It is, yet, another aspect of the present invention to provide a warning system, with a display, notifying a person in a supervisory capacity when an output volume of headphones is too high.

The foregoing and other aspects of the present invention are achieved by a system for controlling a volume output by a set of headphones to prevent harmful sound levels from damaging a user's hearing. The system includes a volume sensor/controller for determining the volume of an audio signal and comparing the volume of the audio signal to a predetermined volume threshold. If the compared volume is outside the volume threshold, the output volume of the headphones is adjusted accordingly. The system also includes a warning indicator that indicates to the user or a person monitoring the user's listening activity that the volume is set too high. Each incident in which the warning indicator is used is stored in a data base for monitoring the long term listening habits of the user. This system is designed to help protect a user's hearing.

In another embodiment, the foregoing and other aspects of the present invention are achieved by a system for controlling a volume output by a set of headphones with a volume sensor controller connected in series between the audio source and the headphones to prevent harmful sound levels from damaging a user's hearing.

In, yet, another embodiment, the foregoing and other aspects of the present invention are achieved by a system for controlling a volume output by a set of headphones receiving wireless audio signals from an audio source to prevent harmful sound levels from damaging a user's hearing.

DETAILED DESCRIPTION OF THE INVENTION

Figure 1:
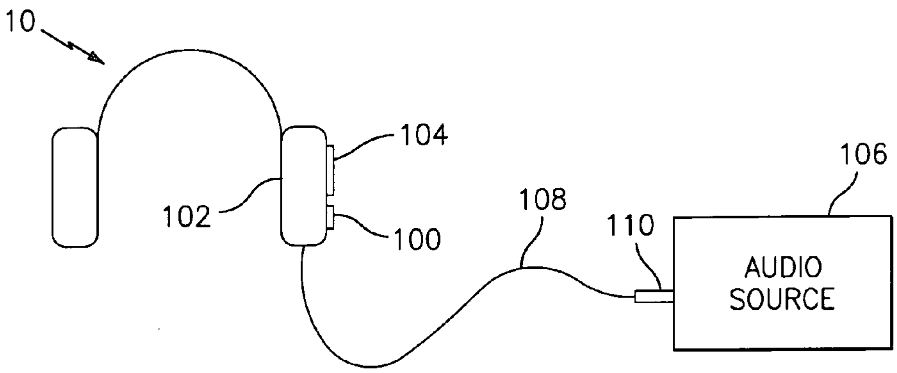
FIG. 1 illustrates a volume regulating and monitoring headset according to a preferred embodiment of the present invention.

FIG. 1 is diagram illustrating an embodiment of the present invention. The embodiment shown by FIG. 1 includes a headset 10 with speaker earpieces 102, is equipped with a volume sensor/controller 100 that receives an incoming audio signal from an audio source 106, such as a stereo, television, radio, microphone, etc. The volume sensor/controller 100 compares the volume of the incoming signal to a predetermined threshold and adjusts the output volume accordingly. The volume sensor/controller 100 will be described herein below in more specific detail with regards to FIG. 2. Also, attached to the headset 10 is a warning display 104, such as a series of LED's, an LCD, or other on-screen display (OSD) that light up or display a message to visually warn a person monitoring the headset user that the individual using the headset has the volume set at a level higher than the predetermined threshold. The warning display 104 may also include an audible warning system, such as a buzzer or chiming device, to audibly warn a person monitoring the headset user that the individual using the headset has the volume set at a level higher than the predetermined threshold.

The headset 10 is connected to an audio source 106 by a cable or wire 108, and connects to the source by jack 110. It is also contemplated that the headset 10 can be connected to audio source 106 in a wireless manner, with a transceiver located in earpiece 102 and a transceiver located in audio source 106.

Figure 2:
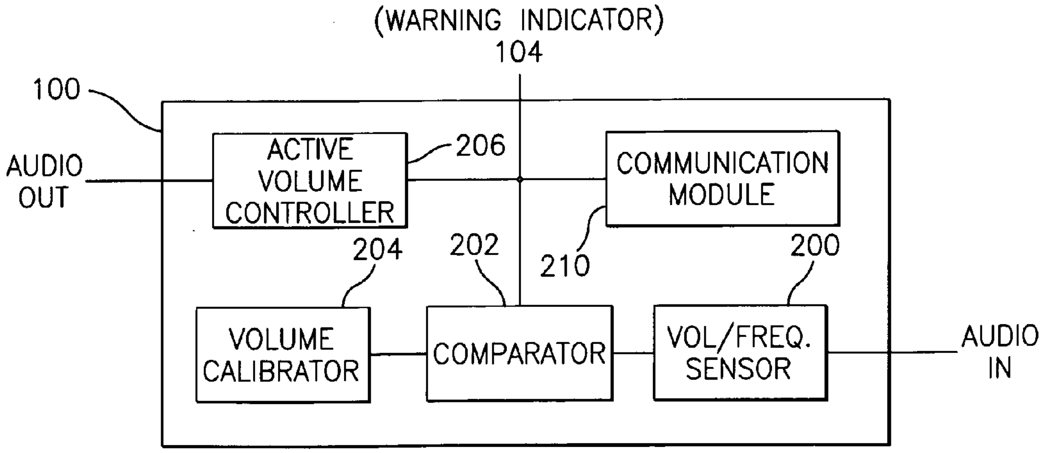
FIG. 2 illustrates a block diagram of the volume sensor/controller as shown in the preferred embodiment of FIG. 1.

FIG. 2 illustrates a block diagram of the volume sensor/controller 100 as described in FIG. 1. The volume sensor/controller 100 includes a volume/frequency sensor 200 for sensing the volume level of the input audio and represents the volume levels as energy functions from frequencies or as some average energy per frequency band, a comparator 202 for comparing the audio input to a volume threshold, a volume calibrator 204 for setting the volume threshold and volume control mode, an active volume controller 206 for automatically reducing an output volume and a communication module 210 for communicating with a remote device and a PC.

The first step in using the volume sensor/controller 100 is to set the volume limits, or more specifically the volume threshold. This operation is done utilizing the volume calibrator 204. The volume calibrator 204 contains different volume settings, and may be done incrementally or in preset steps. The volume calibrator 204 includes a category selector for selecting volume settings suited for different categories of users, and a category data base containing the different categories. Each volume setting has different volume characteristics suited for different users. Some examples of the different types of characteristics include a default category, where the volume is set to a standard level, and an age dependent category, where depending on the user's age the volume thresholds are determined. For example, a young child may have more sensitive hearing than an older adult. Therefore, the volume settings for a user age 3–5 will be much different than a user age 65 and over.

Another type of volume setting is by listener type. For example, listener type can be a volume setting that depends on a type or form of hearing loss or other hearing characteristic of the user. Hearing loss can be related to certain frequency bands. For example, some users have hearing loss at low frequencies and some at high frequencies. Each listener type regulates the volume in accordance with the specific type of hearing loss.

Further, there is a manual controlled setting that allows the user or persons monitoring or caring for the user to set their own volume thresholds. Once a volume threshold has been determined, the mode of the volume control is set to either "automatic" or "manual". In the manual mode, the user or the person monitoring the user, must adjust the volume to be within the threshold limits. In the automatic mode, the output volume is controlled by the volume sensor/controller 100 automatically.

Figure 3:
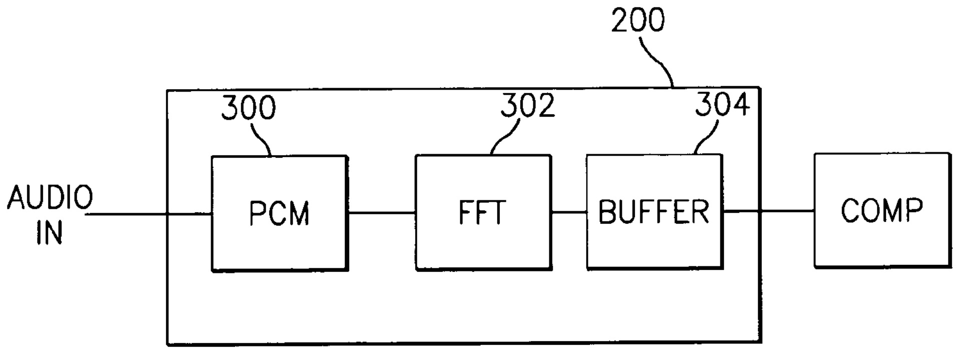
FIG. 3 illustrates a block diagram of the volume/frequency sensor as shown in the volume sensor/controller of FIG. 2.

During operation of the volume/sensor controller 100, an incoming audio signal is received by the volume/frequency sensor 200 as illustrated in FIG. 3. The volume/frequency sensor 200 includes a pulse code modulator (PCM) 300, a fast fourier transformer (FFT) 302, and a buffer 304. The volume/frequency sensor 200 receives an incoming audio signal from an audio source 106 and the PCM 300 modulates it in order for the FFT 302 to represent the audio signal as energy functions of frequencies. The signal processing information is then stored in the buffer 304. The technique for such representation of signals is well described in scientific literature, and other methods of signal processing can also be used as an alternative.

Once the volume thresholds have been determined and the incoming audio signal has been processed by the volume/frequency sensor 200, the comparator 202 compares the processed incoming audio signal stored in the buffer 304 with the volume threshold set in the volume calibrator 204. In the automatic mode, if the incoming audio signal is outside the threshold levels the comparator 202 notifies the active volume controller 206, the warning system 208, and the communication module 210. The active volume controller 206 adjusts the level of the output audio signal accordingly. The warning system 208 receives the signal from the comparator 202 and activates the warning display 104 on the headset 102 to notify the user or the person monitoring the user that the volume is too high. Preferably, in addition to the visual warning display 104, the communication module 210 includes communication hardware for receiving the signal from the comparator 202 and sending a signal to a remote device, such as a hand held remote control, warning the monitor holding the remote device that the user has the volume set too loud. The indication may be a vibration, a visual indication, such as LED's, an audio signal, or a combination to alert the monitoring person. Also, in addition to sending a signal to a remote device, the communication module 210 sends a signal to a transceiver located at a PC to indicate to the person monitoring the user on the PC display that the user has the volume set too loud. In an alternate embodiment, this signal can be sent from a remote location via the Internet or other network. Further, the PC will then store the listener's listening history in a database stored within the PC. In the manual mode, the comparator 202 does not notify the active volume controller 206, but does notify the warning system 208, and the communication module 210. The volume control is to be performed manually, preferably, by using the remote device.

Figure 4:
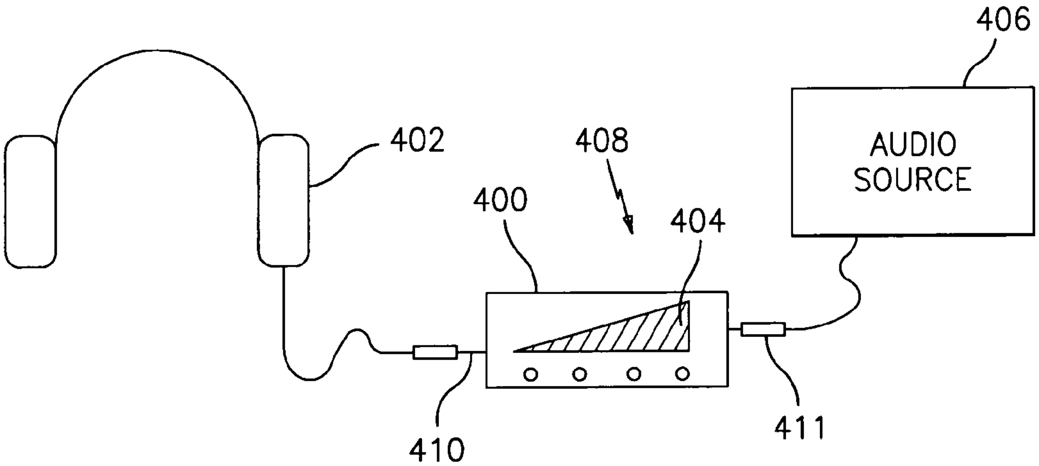
FIG. 4 illustrates a headset according to a second embodiment of the present invention.

FIG. 4 illustrates a another embodiment of the present invention. In this embodiment, instead of being fixed to a headset 102, the volume sensor/control 400 and the warning display 404 are contained in a separate unit 408 allowing the system to work with a regular headset 402. The regular headset plugs into the output jack 410, and the audio source 406 plugs into the input jack 411 of the unit 408. Unit 408 may connect to source 406 through jack 411, or via a wireless connection.

Figure 5:
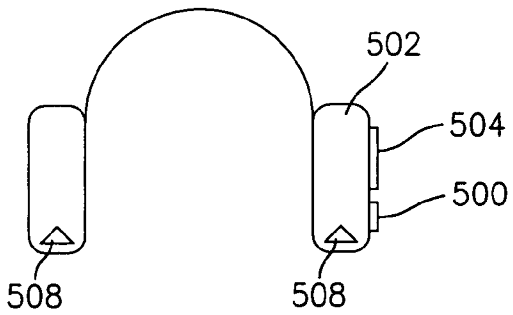
FIG. 5 illustrates a headset according to a third embodiment of the present invention.

FIG. 5 illustrates still another embodiment of the present invention. In this embodiment, a headset 502, similar to the headset 102 described herein above in FIG. 1, is equipped with a microphone 508. The microphone 508 acts as the audio source for the headset 502. The volume sensor/controller 500 and the warning display 504 function as described above. This embodiment of the invention is very useful in noisy situations such as concerts, motor races, and construction zones, in allowing some sound to reach the user under control of the volume sensor/controller 100.

Figure 6:
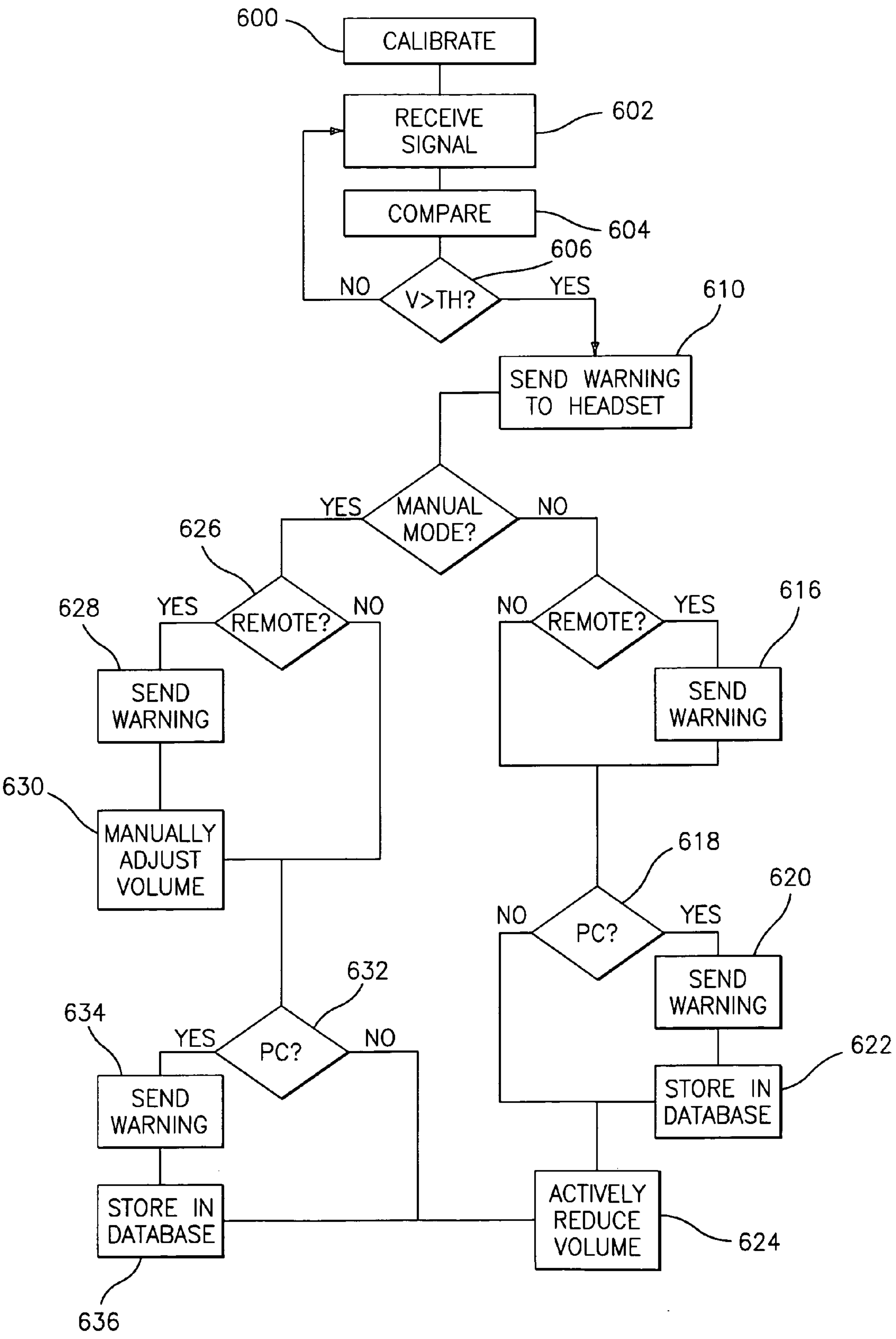
FIG. 6 is a flow chart illustrating a method of operation of a preferred embodiment of the present invention.

FIG. 6 is a flow chart illustrating the method of operation of an embodiment of the present invention. In step 600, a user or a person monitoring the user sets the volume thresholds and the volume control mode in the volume calibrator 204. Next, an incoming audio signal is received and then converted in step 602. The comparator 202 compares the converted signal with a predetermined threshold in step 604 to determine in step 606 if the signal is greater than the threshold. If it is not, then the process returns to step 602 to receive another signal. If it is, in step 610 a warning signal is generated at the headset to notify the user or the person monitoring the user that the volume is set too high. In step 612, it is determined whether the volume control has been set to automatic or manual mode. If the volume control mode is set to automatic mode, in step 614, it is determined whether there is a remote device being used. If yes, in step 616, a warning signal is sent to the remote device. If not, the process goes directly to step 618. In step 618, it is determined whether a PC is being used. If yes, in step 620, a warning signal is sent to the PC. Also, in step 622 the user's listening history stored in a database within the PC is updated. If in step 618 it is determined that no PC is being used, the process skips steps 620 and 622, and goes to step 624 where the output volume is actively reduced accordingly, to be less than or equal to the volume threshold.

If in step 612, it is determined that the volume control mode has been set to the manual mode, in step 626, it is determined whether a remote device is being used. If yes, in step 628, a warning signal is sent to the remote device and in step 630 the person with the remote device adjusts the volume accordingly. If in step 626 it is determined that no remote device is being used, then the process goes directly to step 632 to determine if a PC is being used. If a PC is being used, in step 634 a warning signal is sent to the PC and in step 636 the user's listening history is stored in the database. If no PC is being used, the volume is reduced and the process returns to step 602 to perform the operation with a newly received audio signal.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A system for controlling a volume output by a set of headphones to prevent harmful sound levels from damaging a user's hearing, the system comprising:
- a volume sensor/controller for determining sound levels from an audio source and comparing the predetermined sound levels to a volume threshold, the volume sensor/controller comprising:
  - a volume calibrator for setting the volume threshold, the volume calibrator comprising:
    - a category selector allowing the user to select between different volume controlling settings matching different user characteristics; and
    - a category data base for storing the sound characteristics for the volume controlling settings, the category data base comprising:
      - a default user setting;
      - an age dependent setting;
      - a listener type setting; and
      - a manually controlled setting;
  - a volume/frequency measurement sensor for representing the determined sound levels as energy functions; and
  - a comparator for comparing the determined sound levels with the volume threshold and notifying a warning indicator that the volume threshold has been exceeded; and
- a warning indicator for indicating that the determined sound level is outside the volume threshold.

2. A system for controlling volume output as described in claim 1, wherein the determined sound levels are represented as energy functions according to their respective frequencies.

3. A system as described in claim 1, wherein the warning indicator is fixed to the headphones for indicating when the volume threshold has been exceeded.

4. A system as described in claim 3, wherein the warning indicator comprises a plurality of LED's.

5. A system as described in claim 3, wherein the warning indicator comprises an LCD.

6. A system as described in claim 3, wherein the warning indicator comprises an audio indicator.

7. A category data base as described in claim 1, wherein the listener type setting is configured for setting the volume for a user having a form of hearing loss.

8. A system for controlling a volume output by a set of headphones to prevent harmful sound levels from damaging a user's hearing, the system comprising:
- a volume sensor/controller for determining sound levels from an audio source, comparing the determined sound levels to a volume threshold, and adjusting the volume output of the headphones to a level below the volume threshold if said determined sound level is above the volume threshold, the volume sensor/controller comprising:
  - a volume calibrator for setting the volume threshold and a volume control mode, the volume calibrator comprising:
    - a volume control mode selector allowing the user to select between an automatic or manual volume control mode;
    - a category selector allowing the user to select between different volume controlling settings matching different user characteristics; and
    - a category data base for storing the sound characteristics for the volume controlling settings, the category data base comprising:
      - a default user setting;
      - an age dependent setting;
      - a listener type setting; and
      - a manually controlled setting;
  - a volume/frequency measurement sensor for representing the determined sound levels as energy functions;
  - a comparator for comparing the determined sound levels with the volume threshold; and
  - an active volume controller for controlling the output volume by adjusting the output volume accordingly in an automatic volume control mode.

9. A system for controlling volume output as described in claim 8, wherein the determined sound levels are represented as energy functions according to their respective frequencies.

10. A category data base as described in claim 8, wherein the listener type setting is configured for setting the volume for a user having a form of hearing loss.

11. A volume sensor/controller as described in claim 8, wherein the active volume controller comprises:
- a volume adjuster for adjusting the volume according to the compared energy value; and
- a notifier for notifying a warning system that an adjustment was necessary.

12. A system for controlling a volume output by a set of headphones to prevent harmful sound levels from damaging a user's hearing, the system comprising:
- a volume/frequency measurement sensor for determining sound levels from an audio source and representing the determined sound levels as energy functions;
- a volume calibrator for setting a volume threshold and a volume control mode, the volume calibrator including a category data base for storing sound characteristics for volume control settings, the category data base including a default user setting, an age dependent setting, a listener type setting and a manually controlled setting;
- a comparator for comparing the determined sound levels to the volume threshold; and
- an active volume controller for adjusting the volume output of the headphones to a level below the volume threshold, if a determined sound level is above the volume threshold, and for controlling the volume output by adjusting the volume output of the headphones, according to the volume control mode, in an automatic volume control mode.

13. A system for controlling volume output as described by claim 12, wherein the listener type setting is configured for setting the volume for a user having a form of hearing loss.

14. A system for controlling volume output as described by claim 12, wherein the volume calibrator further comprises a volume control mode selector for allowing the user to select an automatic or a manual control mode.

15. A system for controlling volume output as described by claim 12, wherein the volume calibrator further comprises a category selector for allowing a user to select different volume controlling settings matching different user characteristics.

* * * * *